(12) United States Patent
Ollivier

(10) Patent No.: US 9,101,758 B2
(45) Date of Patent: Aug. 11, 2015

(54) IMPLANTABLE CARDIAC STIMULATION LEAD FOR STIMULATION OF THE LEFT VENTRICLE

(71) Applicant: SORIN CRM S.A.S., Clamart Cedex (FR)

(72) Inventor: Jean-François Ollivier, Villiers le Bacle (FR)

(73) Assignee: SORIN CRM S.A.S., Clamart Cedex (FR)

( * ) Notice: Subject to any disclaimer, the term of this patent is extended or adjusted under 35 U.S.C. 154(b) by 89 days.

(21) Appl. No.: 14/052,459

(22) Filed: Oct. 11, 2013

(65) Prior Publication Data

US 2014/0107756 A1    Apr. 17, 2014

(30) Foreign Application Priority Data

Oct. 12, 2012   (FR) ..................... 12 59761

(51) Int. Cl.
*A61N 1/05* (2006.01)
*A61N 1/375* (2006.01)
*A61N 1/362* (2006.01)

(52) U.S. Cl.
CPC .............. *A61N 1/0592* (2013.01); *A61N 1/059* (2013.01); *A61N 1/362* (2013.01); *A61N 1/375* (2013.01)

(58) Field of Classification Search
CPC ..... A61N 1/05; A61N 1/0534; A61N 1/0551; A61N 1/3754; A61N 1/36017; A61N 1/0558; A61N 1/36146; A61N 1/362; A61N 1/365; A61N 1/37205; A61N 1/057; A61N 1/059; A61N 1/3605; A61N 1/36114
See application file for complete search history.

(56) References Cited

U.S. PATENT DOCUMENTS

| | | | |
|---|---|---|---|
| 7,515,971 B1 | 4/2009 | Doan | |
| 8,121,687 B2 | 2/2012 | Jensen et al. | |
| 2004/0098075 A1 | 5/2004 | Lee | |
| 2005/0080470 A1 | 4/2005 | Westlund et al. | |
| 2006/0106442 A1 | 5/2006 | Richardson et al. | |
| 2006/0258978 A1 | 11/2006 | Vanney | |
| 2008/0294229 A1 | 11/2008 | Friedman et al. | |
| 2012/0136423 A1 | 5/2012 | Ollivier | |

FOREIGN PATENT DOCUMENTS

EP    2 384 784    11/2011

*Primary Examiner* — Rex R Holmes
(74) *Attorney, Agent, or Firm* — Foley & Lardner LLP

(57) ABSTRACT

An implantable cardiac stimulation lead for implantation along the septal wall and/or the free wall of the left ventricular is disclosed. The lead is a microlead formed in its distal portion by a microcable with an active portion comprising a series of exposed areas forming the stimulation electrodes. This lead is implanted by an accessory with a needle having a puncture pointed free end and an opposite end mounted on a gripping end tip, and a releasable device for holding the microcable along the length of the needle. The microlead is introduced by injection of the microcable with penetration of the needle into the wall thickness of the interventricular septum or in the thickness of the free wall of the left ventricle, below the surface and along this wall between the apex region the atrial region.

20 Claims, 3 Drawing Sheets

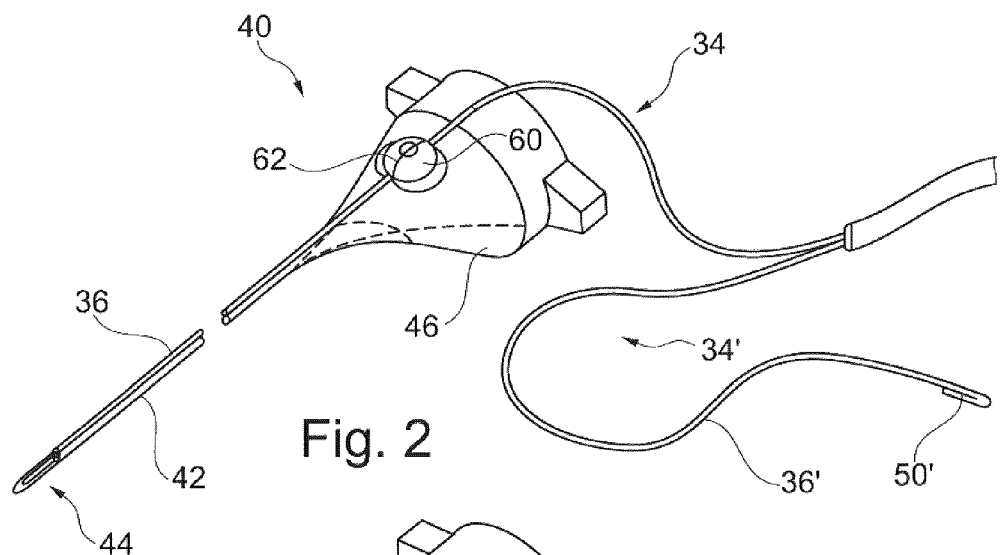
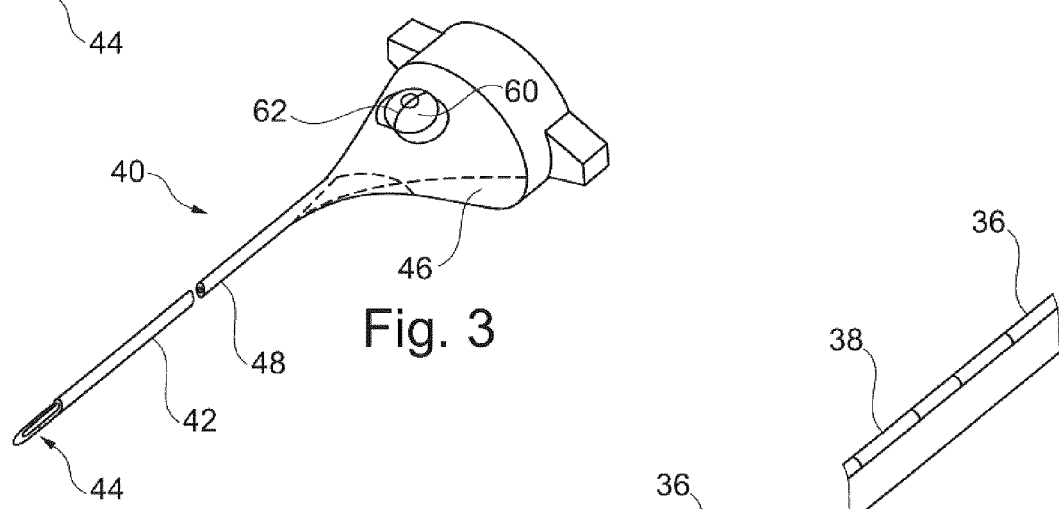
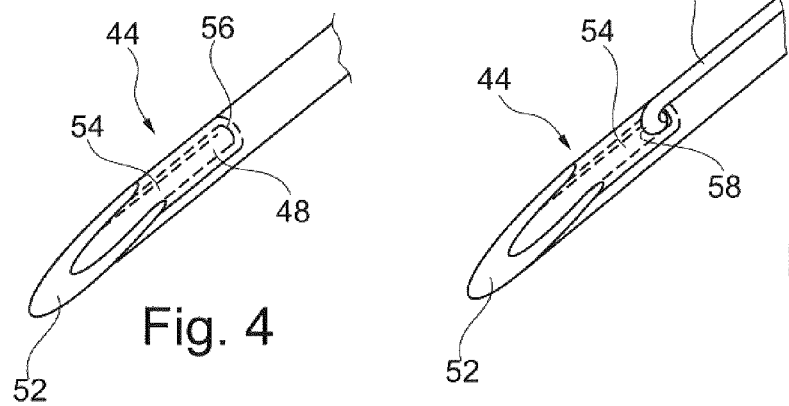
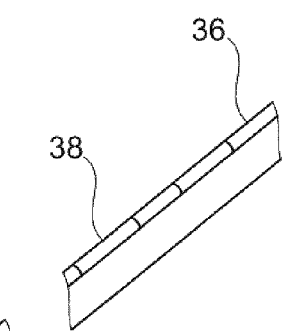

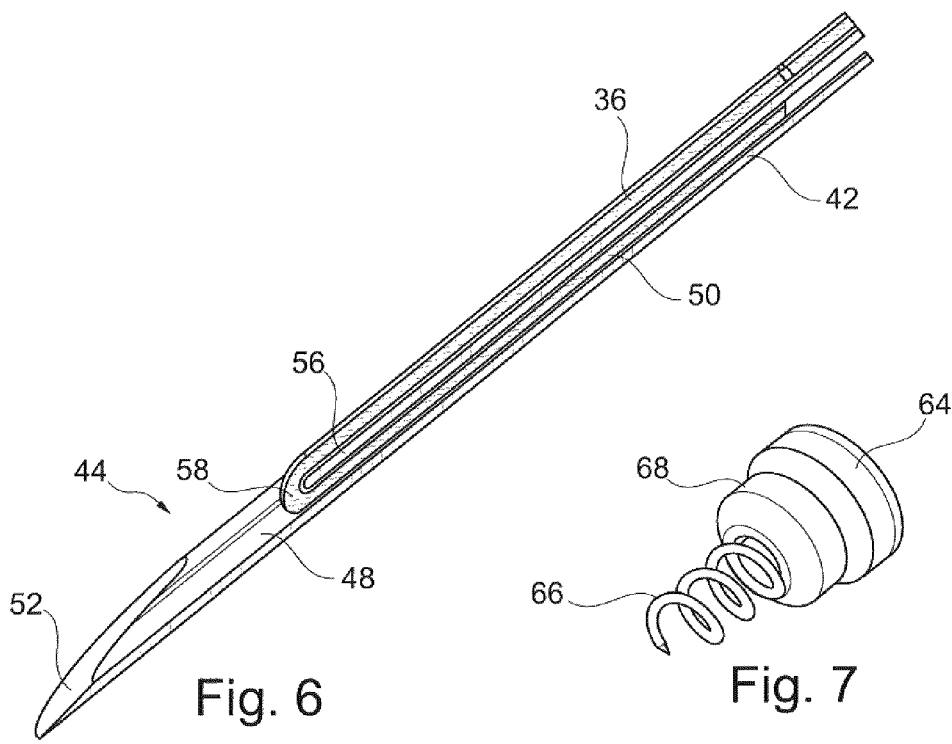
Fig. 6
Fig. 7
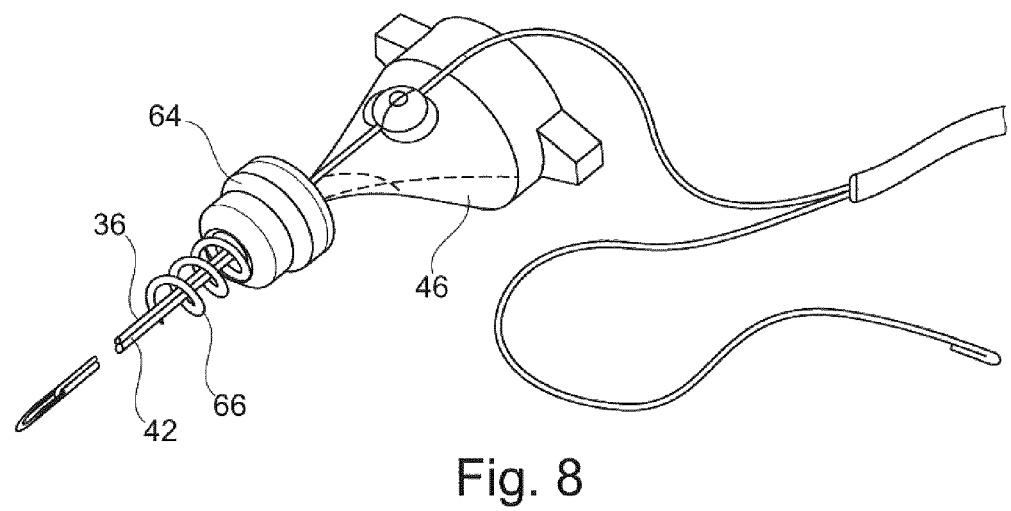
Fig. 8

IMPLANTABLE CARDIAC STIMULATION LEAD FOR STIMULATION OF THE LEFT VENTRICLE

CROSS-REFERENCE TO RELATED APPLICATION

This application claims the benefit of and priority to French Patent Application No. 1259761, filed Oct. 12, 2012, which is incorporated herein by reference in its entirety.

BACKGROUND

The invention relates to left ventricular intracardiac pacing leads.

The invention is in the general context of "active implantable medical devices" as defined by Directive 90/385/EEC of 20 Jun. 1990 the Council of the European Communities, including implants to continuously monitor heart rhythm and deliver as necessary the electrical stimulation, resynchronization or defibrillation pulses to the heart.

Intracardiac "stimulation" leads will mainly be referenced herein, that is to say, leads for the delivery of low-energy pulses used for bradycardia or resynchronization therapies. But the invention also applies to cardioversion/defibrillation intracardiac leads intended to deliver an electric shock of high energy to the heart to try to terminate a tachyarrhythmia. Unless otherwise indicated, the generic terms "stimulation lead (or electrode)" or "pacing/defibrillation lead" may designate any kind of lead used for these purposes, regardless of the type and level of electrical energy delivered.

For right ventricular stimulation, implanting an endocardial lead by the right peripheral venous network is sufficient. However, for left ventricular stimulation, the situation is more complex.

A wide variety of solutions have been proposed for this purpose: lead inserted into the coronary network via the right atrium and the ostium of the coronary sinus, catheter inserted in the right ventricle and positioned against the wall of the interventricular septum, or piercing of the septum then introduction of a lead through the septum until the latter comes into contact with an inner wall of the left ventricle.

Another technique, more difficult to implement and being much more invasive, is to implant epicardial electrodes on the outer myocardium wall, in one or more suitable sites arranged facing the cavity of the left ventricle. The implantation of such a lead is however a very heavy operation, usually requiring general anesthesia and the use of highly invasive surgical techniques. For this reason, this solution is often considered a last resort in case of failure of implantation via the coronary sinus. In addition, the electrical performance is often poor, and it is very difficult to change the implantation site initially chosen and, if necessary, to explant the lead later.

U.S. 2008/0294229 A1 discloses a pacing lead in particular for the left ventricular stimulation by implantation in the thickness of the septal wall, or in the thickness of the left ventricular free wall, below the surface and along this region of this wall between the apex and the atrial region.

U.S. 2005/0080470 A1 describes a specific transthoracic implantation technique of a detection/stimulation lead. However, this technique is particularly invasive, because of the high caliber of the instruments used to cross the chest.

SUMMARY

This invention relates to injecting one or more microcables in the wall thickness of the interventricular septum, and/or respectively in the thickness of the free wall of the left ventricle, in the surface of this wall and along the length thereof extending between the region of the apex and the atrial region, that is to say over the major part of the length of these walls. The microcable is normally intended to stay below the surface of the wall, without leading to the interior of the cavity, nor outside the myocardium except at the point of connection to a lead body connected to the pulse generator.

The microcables thus approximately follow the path of the left branch of the His bundle, which is an internal fast electrical conduction line of the myocardium extending along the interventricular septum near the left ventricle, and then ascending along the free wall of this same left ventricle.

The left branch of the His bundle plays an important role in the mechanism of left ventricular resynchronization, constituting a rapid conduction path (of the order of 4 m/s) from which the conduction of the depolarization wave begins and propagates closer and closer to a substantially slower speed (0.4 m/s) in the remaining myocardial tissue. Preserving, restoring or improving this function has the effect of significantly contributing to the improvement of hemodynamic performance.

The implantation of a microcable here is intended to provide a complete line of conduction, close to the natural route within the myocardium. This conduction line is equipped with one or more stimulation points from which a natural conduction will occur and without delay, even in case of a local left block.

This approach according to the invention of artificially reconstructing the left branch of the His bundle and to apply electrical stimulation at multiple points, is opposed to conventional pacing systems, all of which are designed to focus on a few points of the stimulation, the efficiency of which being possibly quickly altered if the surrounding tissues are not sustainable.

Moreover, as will be seen, from the surgical point of view, the microcables can be injected by a minimally invasive conventional sub-xiphoid (from a needle under the lower sternum area) approach, and only requiring simple instruments.

More specifically, the invention discloses a left ventricular intracardiac pacing lead system, which can be combined with the generator of an active implantable medical device for delivery of cardiac stimulation and/or resynchronization and/or defibrillation pulses.

This system includes an intracardiac lead and an implantation accessory of the lead into the tissue of an internal region of the myocardium.

The lead is intended to be implanted in the tissue of an internal region of the myocardium, penetrating in the thickness of the septal wall, or in the thickness of the left ventricular free wall, and below the surface of the wall along the region between the apex and the atrial region. Specifically, the lead is a microlead consisting, in its active distal portion, of a microcable comprising an electrically conductive core coated with an electrically insulating layer, the active portion comprising a series of exposed areas of the microcable forming the stimulation electrodes electrically coupled together.

Typically, the diameter of the microcable is at most 1 French (0.33 mm), and the free distal end is folded on itself. Moreover, the implantation accessory includes a needle with a puncture pointed free end and an opposite end mounted on a gripping tip, this needle being at least in its distal part a hollow needle having a emergent inner lumen. The folded portion of the distal end of the microcable is inserted into the inner lumen of the needle, and the non-folded portion of the microcable runs against the outer surface of the needle along the latter until the gripping tip. The implantation accessory further comprises a releasable device for holding the microcable, for the support and retention of the microcable along the length of the needle between the puncture end and the gripper tip.

According to this method, it is possible to implant the microlead by simultaneous penetration of the needle and of the microcable carried by this needle in the wall thickness of the interventricular septum or of the free wall of the left ventricle.

According to various exemplary embodiments:
The distal portion of the needle has a channel extending the internal lumen and allows the introduction and the withdrawal of the folded end of the microcable;
At the location of the proximal edge of the channel, the opening of the central lumen of the needle is not sharpened so as to avoid any damage to the folded portion of the microcable at the location of the commissural thereof;
The length of the active part of the microcable forming the series of exposed areas forming the electrodes is between 50 and 150 mm;
The length of the folded portion of the distal end of the microcable is between 2 and 5 mm;
The tip comprises a resilient pad, in particular a silicone pad having a longitudinal slot for clipping the microcable, forming a releasable holding device for the microcable, so as to allow the hold thereof in the stretched state between the pad and the outlet of the inner lumen of the needle;
The electrically conductive core of the microcable comprises a composite structure with a plurality of wires stranded together, at least some of the strands incorporating a core of radiopaque material such as platinum-iridium or tantalum wrapped in a sheath of mechanically enduring material such as NiTi or MP35NLT alloy or vice versa;
The external diameter of the needle is between 0.2 and 0.5 mm;
The assembly further comprises an anchor for anchoring the microcable to a surface of the myocardium;
The anchor can include a helical screw capsule, provided with a mechanism for securing the microcable in an axial region of the capsule;
The outer surface of the screw cap can be formed as a winding drum adapted to receive an excess length of the microcable, or the capsule comprises a resilient member with an axial bore adapted to receive the needle provided with the microcable in the vicinity of the gripping tip;
The anchor may also comprise a glue dot of a biocompatible surgical adhesive; and
The total exposed surface of the exposed areas of the microlead is not more than 6 $mm^2$.

BRIEF DESCRIPTION OF THE FIGURES

FIG. 2 illustrates a lead system according to the invention in a configuration of microcables ready for implantation.

FIG. 3 separately shows the implantation needle of the system of FIG. 2.

FIG. 4 shows the detail of the needle tip of FIG. 3.

FIG. 5 shows details of the tip and of the body of the needle of FIG. 2, with the microcable ready for implantation configuration.

FIG. 6 is a sectional view of the distal end of the needle and of the microcable illustrated in FIGS. 2 and 5.

FIG. 7 shows, in an isolated view, an anchoring capsule for screwing on the epicardium at the outlet of the microcable.

FIG. 8 shows the anchoring capsule of FIG. 7, positioned on the needle of the ready for the implantation system shown in FIG. 2.

DETAILED DESCRIPTION

Figures 1, 9:
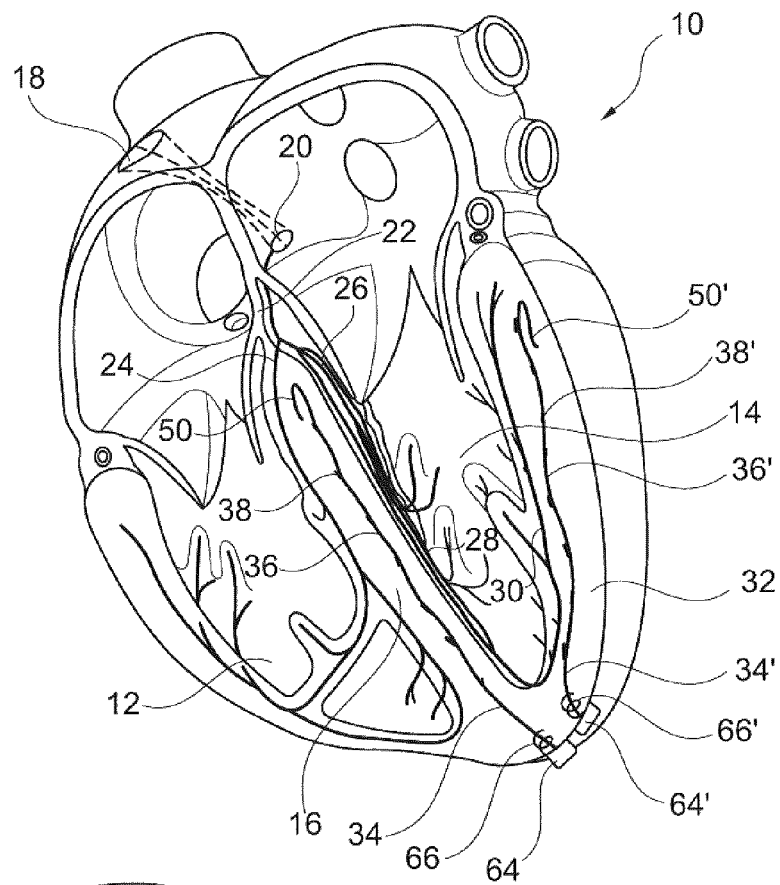
FIG. 1 is a schematic sectional view of the myocardium, showing the different cavities and the main electrical conduction channels.
FIG. 9 is a diagram of the chest and of the heart, showing the access path for the injection of the microcables.

FIG. 1 is a schematic sectional view of the myocardium 10, with the right ventricle 12 and the left ventricle 14 separated by the interventricular septum 16. The interventricular septum 16 has a typical thickness of about 10 to 15 mm and constitutes a significant portion of the cardiac mass.

The depolarization waves that originate in the sinoatrial node 18 are transmitted to the atrioventricular node 20 and then to the His bundle 22, which is divided into two branches extending along the septum 16, with a right branch 24 in the region of the right septal wall 26 and a left branch in the region of the left septal wall 28.

In particular, the left branch 26 is a rapid electrically conductive longitudinal line, with a speed of about 4 m/s. This left branch extends along the left wall 28 of the interventricular septum 16 along the latter to the region of the apex, and then ascends in 30 along the free wall of the left ventricle 32, approximately up to the region of the atrium.

In an exemplary embodiment, several microleads 34, 34', the respective active ends of which are made of micro-cables 36, 36', are each provided with one or more stimulation electrodes 38, 38', preferably a large number of individual very small electrodes.

In some embodiments more than two microleads may be provided. In some embodiments several microleads may be implanted in the septal wall and/or the free wall of the left ventricle. Such a proliferation of microleads lead to form around the left ventricle a "mesh" distributing in the heart muscle a microelectrode array themselves carried by a plurality of microcables radiating from the apex.

The microcables with their electrodes allow to artificially reconstruct a conduction path parallel to the left branch of the His bundle and to excite in a plurality of points the left ventricle both in the side of the septal wall and in the side of the free wall.

According to an exemplary embodiment, the total area of the electrodes of a microlead does not exceed 6 $mm^2$, a value of the same order as the active surface of a standard endocardial lead. The very small diameter of the microcable (typically 0.1 mm) allows designing electrodes on a total length of 20 mm without exceeding the above value of 6 $mm^2$ of exposed surface: if the length of a single electrode is reduced to 0.5 mm, this allows a potential for forty electrodes distributed along a same microcable, so there is a very significant increase of the stimulation points, which are also in direct contact with tissue, therefore with excellent transmission quality of the pacing pulses of the electrode to the tissue.

In one embodiment, the microcable may however be completely exposed in its distal active part, a configuration thus corresponding to a single very long electrode.

The microcable may comprise a core comprising a plurality of composite strands stranded together, e.g. with a central strand surrounded by six peripheral strands. Each composite strand is itself made up of a strand the core of which is made of an alloy such as MP35NLT, wrapped in a sheath of platinum-iridium (for radio-opacity and biostability). These different strands are commercially available, for example from Fort Wayne Metals Company Inc., Fort Wayne, USA, and are used in the medical field.

The microcable is coated with a thin insulation layer, of the order of 25 µm thick. The characteristics required for this layer are: fatigue resistance, electrical isolation, long-term biocompatibility, biostability, and the possibility of transformation and implementation compatible with the conductor of the core cable. To achieve this insulation layer, materials with high chemical inertness may be preferred, as fluoropolymers, which also have very good insulation. Among these compounds, mention may in particular be made to ETFE (ethylene tetrafluoroethylene). The methods for producing the insulation layer of the core cable are, for example, co-extrusion on the conductor or the heating of a heat shrinkable tube.

The active part of the microcable includes in the illustrated example a plurality of exposed parts forming a succession of individual electrodes, together forming a network connected in series to multiply the points of stimulation. This multiplies the opportunities for points of contact with the tissues and thus ensures multi-zone dissemination of the stimulation energy at several points of the left ventricle. The electrodes are formed for example by plasma ablation of the parylene layer. To improve the electrical performance, these zones can further be coated with titanium nitride for example.

Due to the low cumulative active surface, the benefits of a "high current density" lead are met, in terms of both physiological efficacy of stimulation and lower energy consumption—this while maximizing the extent of the zone of physical, thus electrical, contact with excitable tissues. Moreover, the myocardial localization of the electrodes reduces the risk of phrenic nerve stimulation.

Referring now to FIGS. 2-9, the method of implantation of these microcables 36, 36' by a hypodermic needle accessory used to directly introduce or "inject" the microcable in the myocardial tissue is described.

The implantation accessory, referenced 40, comprises a hollow needle 42 having a pointed distal end 44, and mounted at its opposite end to a gripping proximal end 46. The gripping tip 46 is preferably a connection tip of the Luer lock type for direct mounting on a syringe that is used as a manipulation handle of the system, with further possibility of injecting a contrast medium or physiological serum.

The needle has a typical diameter of 0.2 to 0.5 mm and can be made of a superelastic material such as nitinol, to increase its resistance to kinking.

This needle 42 has the function of providing mechanical support to the microcable 36 which, because of its extreme thinness (typically 0.1 mm, about the thickness of a human hair), cannot be directly implanted in the myocardial wall. The end of the microcable 36 or 36' is folded over itself respectively in 50, 50' of about 2-5 mm to form a hook fastening introduced, as can be seen in FIGS. 5 and 6, in the inner lumen 48 of the needle 42.

The distal portion 44 of the needle 42 has a sharpened end 52 to allow a thin cutting of tissues without tearing them, minimizing their damage and ensuring rapid healing. This region also has a channel 54 extending the inner lumen 48 to allow the introduction and removal of the folded end 50 of the microcable 36. The proximal edge 56 of this cutting is, however, not sharpened to avoid damaging of the commissure 58 microcable.

The needle body is manually conformable by the physician in order to match the morphology of the walls to be punctured.

The microcable 36, hooked to the needle at its distal end by the folded end 50, is slightly maintained under tension along said needle, being locked in translation by clamping in an elastic pad 60 provided on the gripping tip 46. The elastic pad 60 is for example a silicone pad comprising a longitudinal slot 62 in which the microcable 36 is force-clipped. To enhance the temporary connection between the needle and the microcable, the latter may be wrapped around the body of the needle before being clipped into the slot 62 of the silicone pad 60.

As shown in FIG. 2, beyond this plot 60 the microcable proximally extends and joins the other microcable 36'. The two microcables are combined in a traditional lead body, provided at its other end (proximal end of the lead body, not shown) of a connector to be connected to generator housing, according to known methods.

It is important to note that the method and the implantation tool described above allow to have a "ready to use" lead, easy to use, not requiring:
  A medical intervention of the physician to make a connection microcable/lead body; and
  A peeling of the puncture needle.

Electrically speaking, both microcables 36, 36' can either be connected together or connected to different poles of the generator, which in this case allows setting a delay between the stimulation of the two (septal and free) walls of the left ventricular. In the case of a large number of microcables, the end of the lead body may be provided with an electronic multiplexer for controlling the energy distribution (sequence, type of signal, energy level) of the different microcables.

Certain embodiments of the inventions are not limited to monopolar microcables. In some embodiments, for example, the microcables may be multipolar. The microcable may include a plurality of individually insulated elementary microcables and stranded together, in order to polarize certain electrodes (or groups of electrodes) independently of each other. Such a multipolarity may allow a certain amount of "electronic repositioning", which may offer many possibilities for stimulation of tissue through the selection and polarization of certain conduction lines among the several included in the microlead, and for programming stimulation or defibrillation zones according to the therapy.

FIGS. 7 and 8 illustrate an refinement consisting of adding to each microcable attachment to the epicardium, at the emerging point, an anchoring capsule 64 locally implanted at this point (FIG. 1). The role of this anchoring capsule is dual:
  Separating the portion of the microcable implanted in the myocardium of the rest of the lead, notably to avoid after implantation and before the end of the intervention a microcable displacement consecutive to accidental pulling of the lead body; and
  Managing the output angle (typically the perpendicularity) of the microcable near the emerging point, avoiding large amplitude movements around this strongly curved, and consequently, constraint area (even if compliance loops are provided in the emerging part of the microlead to absorb stress and movement between the emerging point and the lead body itself).

The anchoring capsule 64 illustrated FIG. 7 includes a body having a helical screw fastener 66. In a first embodiment, the anchoring capsule 64 is screwed close to the emerging point of the microcable after injection of the latter. The protruding part of the microcable is then wound on a portion 68 of the anchoring capsule shaped as winding and is then clipped into a slot formed on the appropriate output of the capsule body 64, leaving a minimum clearance between the emerging point and the capsule.

In another possible embodiment, shown in FIG. 8, the anchoring capsule 64 is pre-mounted on the body of the needle 42 in the proximal area of the latter. After the needle is in position and the microcable is injected into the myocardium, the capsule is then threaded, and then the needle is withdrawn. The microcable is then clamped in the axial bore of the capsule 64 wherein it is held in place, despite the various stresses which may be applied to the emerging portion of the lead.

Other mechanisms for keeping up the microcable at its emerging point can be provided, among which may be mentioned the filing of a dot of glue of a biocompatible surgical adhesive, such as Bioglue of the CryoLife Inc. company, USA.

One of the major advantages of the invention is the ability to inject microcables by a minimally invasive surgery, typically a sub-xiphoid approach and only using conventional accessories.

As shown in FIG. 9, the tip 46 of the needle 42 is mounted on a syringe body 70. During injection, the microcable is maintained along the needle and blocked in translation by the clip in the resilient pad 60, thereby preventing the release of the hook formed by the folded end 60. This configuration allows some back and forth movements of the needle if necessary to refine its trajectory in the heart muscle.

The tip of the needle can be provided with identification features (radio-opaque marker, ultrasound, etc.) to guide the operator during the operation, in particular to ensure that the chosen path predominantly remains in muscle. It is also possible to inject contrast medium by the syringe through the needle, for the same purpose.

The needle having reached its final position, the operator releases the microcable of the elastic pad 60 which clipped it, and pulls the needle. The body of the microcable is opposed to return movement under the effect of tissue compression, thereby releasing the folded end 50 which then permanently fixes by hook effect, the microcable.

The presence of the hooks 50, 50' formed by the folded portion of the distal end of the microcables 36, 36' provides good resistance to extraction during the injection operation, and then under the effect of internal stresses due to heartbeat.

However, if it is desirable to completely remove the microcable, sustained external traction effort will effectively straighten the kink, allowing the withdrawal of the microcable. The system of the invention can thus be easily explanted and without major damage to the tissues, unlike almost all of the known systems for left ventricle stimulation.

The invention claimed is:

1. An intracardiac lead system for stimulation of a left ventricle, which can be combined with a generator of an active implantable medical device for delivery of pacing and/or resynchronization and/or defibrillation pulses, this system including:
    a lead for implantation in tissue of an internal region of a myocardium, by penetration in a thickness of a wall of an interventricular septum or in a thickness of a free wall of the left ventricle, below a surface and along a wall of a region between an apex region and an atrial region;
    this lead being a microlead comprising, in its active distal portion, a microcable having an electrically conductive core coated with an electrically insulating layer, the active portion comprising a series of exposed areas forming stimulation electrodes the microcable electrically connected together, and
    an accessory for implantation of the lead, wherein a free distal end of a microcable is folded upon itself, wherein the implantation accessory comprises a needle with a puncture tip and an opposite end mounted to a gripping tip, this needle being at least in its distal portion a hollow needle having an emerging inner lumen, wherein a folded portion of the distal end of the microcable is inserted into the inner lumen of the needle, and an unfolded portion of the microcable extends against an outer surface of the needle along thereof to the gripping tip;
    wherein the implantation accessory further comprises a releasable device for holding the microcable, for support and retention of the microcable along a length of the needle between the puncture tip and the gripping tip, so as to allow the implantation of the microlead by simultaneous penetration of the needle and of the microcable carried by the needle in the wall of the interventricular septum or of the free wall of the left ventricle.

2. The system of claim 1, wherein the distal portion of the needle has a channel extending from the inner lumen and adapted to allow the introduction and removal of the folded end of the microcable.

3. The system of claim 2, wherein, at the location of a proximal edge of the channel, the opening of a central lumen of the needle is not sharpened so as to avoid damage to the folded portion of the microcable at a location of a corner thereof.

4. The system of claim 1, wherein a length of the active portion of the microcable comprising the series of exposed areas forming electrodes is between 50 and 150 mm.

5. The system of claim 1, wherein the length of the folded portion of the distal end of the microcable is between 2 and 5 mm.

6. The system of claim 1, wherein the gripping tip comprises a resilient stud forming said releasable holding device of the microcable, so as to allow the hold of the microcable in the stretched state between the resilient stud and the emerging of the inner lumen of the needle.

7. The system of claim 6, wherein the resilient stud is a silicone pad material having a longitudinal slot for clipping the microcable.

8. The system of claim 1, wherein the electrically conductive core of the microcable comprises a composite structure with a plurality of strands stranded together, at least some of the strands being strands incorporating a core of radiopaque material, such as platinum-iridium or tantalum wrapped in a sheath of a mechanically enduring material such as NiTi or a MP35NLT alloy or vice versa.

9. The system of claim 1, wherein an outer diameter of the needle is between 0.2 and 0.5 mm.

10. The system of claim 1, further comprising an anchor for anchoring the microcable to a surface of the myocardium.

11. The system of claim 10, wherein the anchor comprises a capsule with a helical screw provided with a securing mechanism for securing the anchor to the microcable in an axial region of the capsule.

12. The system of claim 11, wherein the outer surface of the screw capsule is designed as a winding drum adapted to receive an excess length of the microcable.

13. The system of claim 11, wherein the screw capsule comprises a resilient member with an axial bore adapted to receive, near the gripping tip, the needle provided with the microcable.

14. The system of claim 10, wherein the anchor comprises a surface for coupling the lead to the anchor via a biocompatible surgical adhesive.

15. The system of claim 1, wherein the total area of the exposed areas of the microlead is at most 6 mm$^2$.

16. A method for use with a lead system for stimulation of tissue, the method comprising:
    providing a lead for implantation in the tissue, the lead comprising a microcable carrying at least one electrode;

folding a free distal end of the microcable;

providing an accessory for implantation of the lead, the accessory comprising a needle having a hollow portion at its pointed end;

inserting the folded distal end of the microcable into the hollow portion;

extending a remainder of the microcable along an outer surface of the needle; and using a releasable device for holding the microcable at an location on the accessory spaced apart from the pointed end of the needle.

17. The method of claim 16, wherein the releasable device holds the microcable under some tension along the length of the needle.

18. The method of claim 17, further comprising:
using the accessory to insert the needle into the issue; and
withdrawing the needle, while leaving the microcable in the tissue.

19. The method of claim 18, further comprising:
inserting an anchor into an portion of tissue; and
securing a portion of the microcable to the anchor.

20. An accessory for implanting a lead in tissue, comprising:

a body having a needle end and a gripping end;

a needle held by the body at the needle end, wherein the needle is at least partially hollow and sized to receive a folded end of the lead;

wherein the body includes a holding device which holds the lead against the needle during insertion of the needle carrying the folded end of the lead into the tissue.

\* \* \* \* \*